(12) United States Patent
Kunita et al.

(10) Patent No.: US 8,056,175 B2
(45) Date of Patent: Nov. 15, 2011

(54) TOOTHBRUSH DEVICE

(75) Inventors: Tomohiro Kunita, Hikone (JP); Suehisa Kishimoto, Hikone (JP)

(73) Assignee: Panasonic Electric Works, Co., Ltd., Kadoma-Shi, Osaka (JP)

( * ) Notice: Subject to any disclaimer, the term of this patent is extended or adjusted under 35 U.S.C. 154(b) by 531 days.

(21) Appl. No.: 12/359,420

(22) Filed: Jan. 26, 2009

(65) Prior Publication Data

US 2009/0188057 A1    Jul. 30, 2009

(30) Foreign Application Priority Data

Jan. 28, 2008 (JP) ................ 2008-016940

(51) Int. Cl.
*A46B 15/00* (2006.01)
*A61C 17/22* (2006.01)

(52) U.S. Cl. ........... 15/22.1; 15/105; 15/167.1; 604/20; 607/79

(58) Field of Classification Search .......... 15/22.1, 15/105, 167.1; 601/21; 604/20; 607/79
See application file for complete search history.

(56) References Cited

U.S. PATENT DOCUMENTS

| | | | |
|---|---|---|---|
| 4,726,806 A | 2/1988 | Hukuba | |
| 5,099,536 A | 3/1992 | Hirabayashi | |
| 5,133,102 A | 7/1992 | Sakuma | |
| 2002/0174498 A1 | 11/2002 | Li | |
| 2003/0000031 A1 | 1/2003 | Zhuan | |
| 2008/0083074 A1* | 4/2008 | Taniguchi et al. | 15/22.1 |
| 2008/0086189 A1* | 4/2008 | Taniguchi et al. | 607/134 |
| 2008/0183249 A1* | 7/2008 | Kitagawa et al. | 607/79 |

FOREIGN PATENT DOCUMENTS

| JP | 09-140453 | 6/1997 |
|---|---|---|
| WO | WO9009123 A1 | 8/1990 |

* cited by examiner

*Primary Examiner* — Mark Spisich
(74) *Attorney, Agent, or Firm* — Workman Nydegger

(57) ABSTRACT

A toothbrush device including a brush member and a grip. The brush member includes an electric terminal accommodation chamber and an electric terminal plate accommodated in the electric terminal accommodation chamber. The electric terminal plate includes a contact, which comes into contact with a contact portion of a coupler shaft of the grip through a window providing communication with a receptacle of the brush member. The brush member includes a holding portion supporting the coupler shaft. The receptacle includes a fastener mount portion and an engaging piece which cooperates with the fastener mount portion to hold the coupler shaft therebetween. The engaging piece and the contact portion are arranged at the same side of the axis of the coupler shaft. The fastener mount portion is arranged opposite the contact portion with respect to the axis of the coupler shaft.

6 Claims, 2 Drawing Sheets

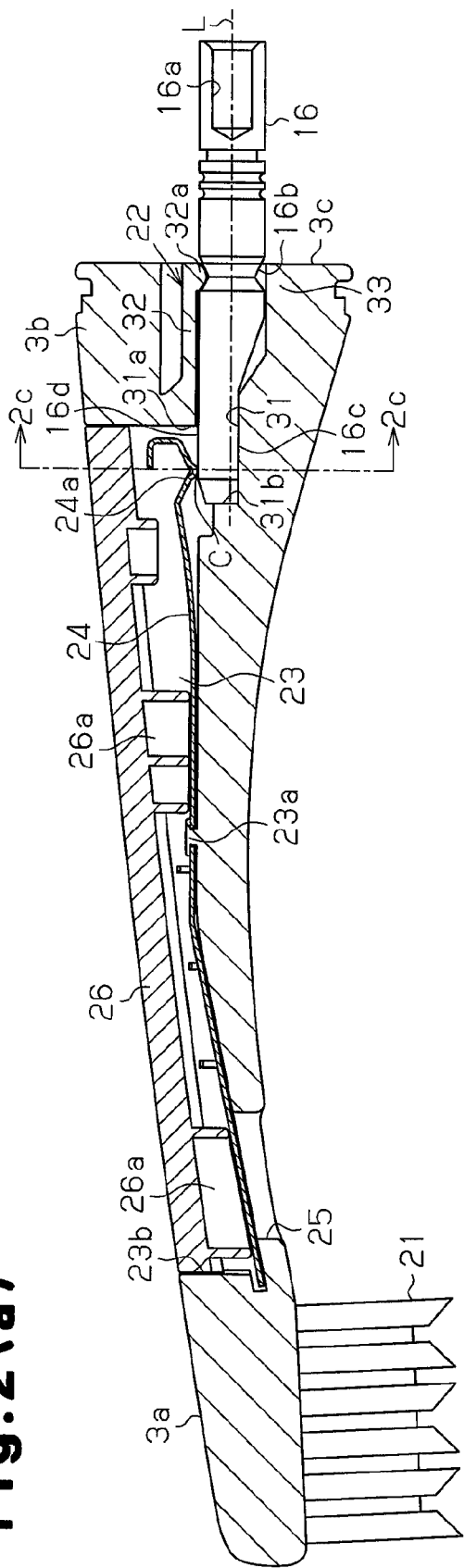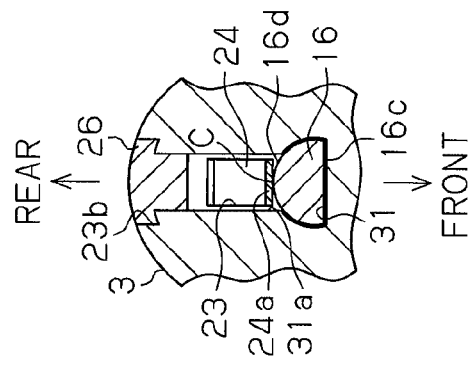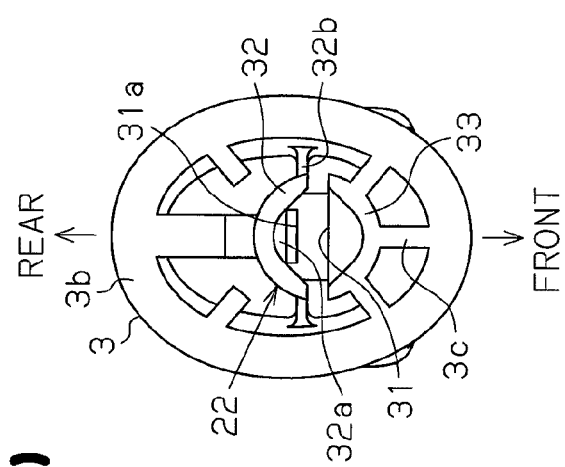

TOOTHBRUSH DEVICE

CROSS-REFERENCE TO RELATED APPLICATIONS

This application claims the benefit of Japanese Patent Application No. 2008-016940, filed on Jan. 28, 2008, the entire contents of which are incorporated herein by reference.

TECHNICAL FIELD

The present invention relates to a toothbrush device that uses a potential gradient to improve a plaque removal effect.

BACKGROUND ART

Japanese Laid-Open Patent Publication No. 9-140453 describes an example of a toothbrush device that uses a potential gradient to improve a plaque removal effect. Such a toothbrush device includes a grip (main body) and an exchangeable brush member. A basal end of the brush member is connected to a distal end of the grip. A coupler shaft projects from the distal end of the grip. The brush member includes a receptacle formed in the basal end. The coupler shaft is inserted into the receptacle. Further, the coupler shaft has a basal end electrically connected to one of the electrodes of a battery, which is retained in the grip. When attaching the brush member to the grip, a distal end of the coupler shaft moves into the receptacle of the brush member to a position at which an electric terminal plate is located. An electric terminal accommodation chamber accommodates most of the electric terminal plate. However, the electric terminal plate has a contact that is exposed through an opening, which communicates the electric terminal accommodation chamber and the receptacle. Through this opening, the contact of the electric terminal plate resiliently contacts the distal end of the coupler shaft. The other electrode of the battery in the grip is electrically connected to an exterior electrode portion arranged on an outer surface of the grip. When a person brushes his or her teeth, the person's hand holding the grip touches the exterior electrode portion. This forms a closed circuit when the brush member comes into contact with the person's mouth. As a result, the battery sends a very weak current into the mouth via the coupler shaft and the electric terminal plate.

SUMMARY OF THE INVENTION

In the toothbrush device of the above publication, the distal end of the coupler shaft comes into resilient contact with the electric terminal plate inside the receptacle. However, the brush member easily moves in its axial direction and is apt to dislodge from the grip. To prevent the brush member from falling out of the grip, the contact of the electric terminal plate may be arranged so as to resiliently contact a lateral side surface of the distal end of the coupler shaft when inserted in the receptacle.

In this case, the opening that communicates the electric terminal accommodation chamber and the receptacle would be located at a position facing toward the lateral side surface of the distal end of the coupler shaft. Thus, the lateral side surface of the distal end of the coupler shaft would not be supported by the wall of the receptacle. In this case, an elastic hooking piece, which is snap-fitted to the coupler shaft, may be arranged at the inlet of the receptacle so that the elastic force of the locking piece moves the lateral side surface of the distal end of the coupler shaft, which is not supported by the wall of the receptacle, toward the opening. However, this may cause inclination or rattling of the brush member.

The present invention provides a toothbrush device that prevents rattling of the brush member.

One aspect of the present invention is a toothbrush device provided with a grip including a coupler shaft and a power supply. A brush member includes a receptacle for receiving the coupler shaft for connection with the grip. The brush member further includes an electric terminal accommodation chamber and an electric terminal plate accommodated in the electric terminal accommodation chamber. The electric terminal plate includes a contact, which comes into contact with a contact portion of the coupler shaft through a window providing communication with the receptacle, and the electric terminal plate is supplied with power from the power supply through the contact and the coupler shaft. The brush member includes a holding portion which supports the coupler shaft at a side opposite the contact portion in the receptacle. The receptacle has an inlet including an engaging piece, which upon completion of insertion of the coupler shaft resiliently returns to substantially its original shape and engages the coupler shaft, and a fastener mount portion, which faces toward the engaging piece, and the engaging piece cooperates with the fastener mount portion to hold the coupler shaft therebetween. The engaging piece and the contact portion are arranged at the same side of an axis of the coupler shaft. The fastener mount portion is arranged opposite the contact portion with respect to the axis of the coupler shaft.

In one embodiment, the grip includes a drive unit which reciprocates the coupler shaft along the axis of the coupler shaft.

In one embodiment, the fastener mount portion and the holding portion are arranged at the same side of the axis of the coupler shaft.

In one embodiment, the brush member has a front side including a brush, the fastener mount portion is arranged at the front side with respect to the axis of the coupler shaft, and the engaging piece and the contact portion are arranged at a rear side, which is opposite to the front side, with respect to the axis of the coupler shaft.

In one embodiment, the fastener mount portion and the holding portion are arranged at the front side with respect to the axis of the coupler shaft.

In one embodiment, the engaging piece is a resilient hook, and the fastener mount portion is a rigid body.

Other aspects and advantages of the present invention will become apparent from the following description, taken in conjunction with the accompanying drawings, illustrating by way of example the principles of the invention.

BRIEF DESCRIPTION OF THE DRAWINGS

The invention, together with objects and advantages thereof, may best be understood by reference to the following description of the presently preferred embodiments together with the accompanying drawings in which:

FIG. 2(a) is a cross-sectional view of a brush member together with a coupler shaft;

FIG. 2(b) is a schematic diagram showing a basal end surface of the brush member without the coupler shaft; and FIG. 2(c) is a partial cross-sectional view taken along line 2c-2c.

DETAILED DESCRIPTION OF THE PREFERRED EMBODIMENTS

Figure 1:
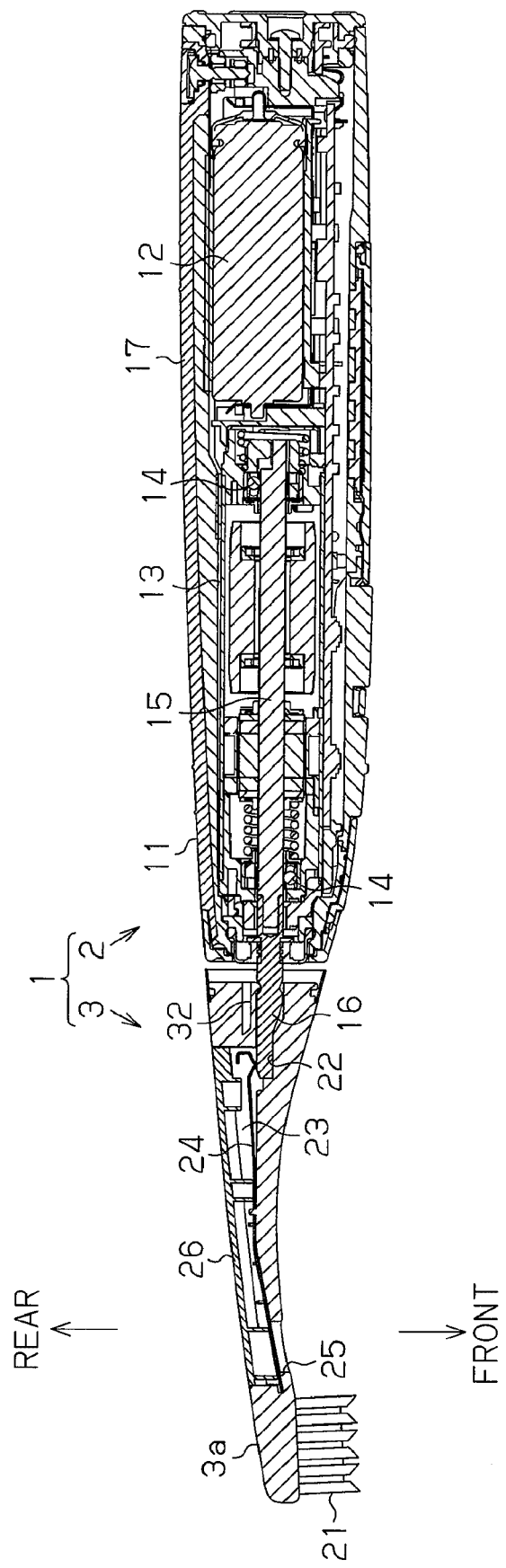
FIG. 1 is a cross-sectional view of a toothbrush device according to an embodiment of the present invention.

A toothbrush device according to an embodiment of the present invention will now be discussed.

As shown in FIG. 1, the toothbrush device 1 includes a grip 2 (main body) and a brush member 3. The brush member 3 is detachably connected to the distal portion of the grip 2.

The grip 2 includes an elongated tubular housing 11. The housing 11 has a basal portion retaining a battery 12. Further, the housing 11 has a distal portion retaining a linear motor 13, which serves as a drive unit. The linear motor 13 is driven when supplied with power from the battery 12. The linear motor 13 includes a slide shaft 15. Two bearings 14, which are fixed in the housing 11, support the two ends of the slide shaft 15. In the housing 11, a basal end of a coupler shaft 16 is coaxially fixed to a distal end of the slide shaft 15. The coupler shaft 16 projects from a distal portion of the housing 11. The slide shaft 15 and the coupler shaft 16, when driven by the linear motor 13, generate fine vibrations at high speeds. Further, the slide shaft 15 and the coupler shaft 16 are each conductive. An exterior electrode portion 17 is arranged on an outer surface of the housing 11.

Referring to FIG. 2(a), the coupler shaft 16 includes a basal portion in which a fastening hole 16a is formed, an intermediate portion in which a V-shaped annular groove 16b extending in the circumferential direction is formed, and a distal portion that is distal from the intermediate portion. The distal portion of the coupler shaft 16 has a distal surface including a flat surface 16c and a curved surface 16d. The distal end of the slide shaft 15 is fitted to the fastening hole 16a of the coupler shaft 16. As shown in FIG. 2(c), the distal portion of the coupler shaft 16 has a D-shaped cross-section. The part of the coupler shaft 16 that extends from the distal portion to the annular groove 16b is inserted into the brush member 3.

The brush member 3 includes a basal portion to which the coupler shaft 16 is attached, a head 3a provided with a brush 21, and a neck gradually curved from the basal portion to the head 3a. The basal portion and the neck may each have a crosssection that is, for example, elliptical. The head 3a may have a cross-section that is, for example, rectangular. Hereafter, the side of the head 3a from which the bristles of the brush 21 extend will be referred to as the front side of the brush member 3 or toothbrush device 1, and the opposite side will be referred to as the rear side of the brush member 3 or toothbrush device 1.

The basal portion of the brush member 3 includes a receptacle for receiving and fixing the coupler shaft 16. When the coupler shaft 16 is inserted into the receptacle 22, the flat surface 16c of the coupler shaft 16 faces frontwards. An electric terminal accommodation chamber 23 is defined in the neck of the brush member 3. The electric terminal accommodation chamber 23 is in communication with the receptacle 22 at a position corresponding to the curved surface 16d of the coupler shaft 16. The curved surface 16d of the coupler shaft 16 is at least partially arranged in the electric terminal accommodation chamber 23. The electric terminal accommodation chamber 23 extends from the receptacle 22 to near the head 3a of the brush member 3. An electric terminal plate 24, which is elongated and conductive, is accommodated in the electric terminal accommodation chamber 23.

The electric terminal plate 24 extends along the inner surface of the electric terminal accommodation chamber 23. Further, the electric terminal plate 24 has a longitudinal central portion, which is fixed to the electric terminal accommodation chamber 23 by a resin pin 23a. The electric terminal plate 24 also has a basal portion, which includes a contact 24a extending toward the distal surface of the coupler shaft 16. In a state in which the coupler shaft 16 is not received in the receptacle 22, the contact 24a of the electric terminal plate 24 is located at a position where it is close to or in contact with the inner surface, or holding portion 31, of the receptacle 22.

Insertion of the coupler shaft 16 into the receptacle 22 resiliently moves the electric terminal plate 24 with the distal portion of the coupler shaft 16. As a result, the contact 24a resiliently comes into contact with the curved surface 16d of the coupler shaft 16. The brush member 3 includes a hole 25 that opens to the front near the head 3a. The hole 25 is in communication with the electric terminal accommodation chamber 23. The distal portion of the electric terminal plate 24 is exposed through the hole 25.

The rear side of the brush member 3 includes a groove 23b, which extends longitudinally throughout the entire neck. A cover 26 seals the groove 23b. In a state in which the cover 26 is removed from the groove 23b, the electric terminal plate 24 is set into the electric terminal accommodation chamber 23 through the groove 23b. The cover 26 includes projections 26a, such as pins or fins, which press the electric terminal plate 24 toward the inner surface of the electric terminal accommodation chamber 23. When the groove 23b is sealed by the cover 26, the projections 26a prevent displacement of the electric terminal plate 24.

[Fastening Structure of Receptacle]

The holding portion 31, which comes into contact with or holds the distal portion of the coupler shaft 16, is located at an inner part of the receptacle 22. A engaging piece 32 and a fastener mount portion 33 are arranged at the inlet of the receptacle 22. The engaging piece 32 cooperates with the fastener mount portion 33 to hold and catch the longitudinal middle part of the coupler shaft 16 therebetween. The fastener mount portion 33 and the holding portion 31 are formed to be continuous with each other. The fastener mount portion 33 and the holding portion 31 are arranged, for example, at the front side of the brush member 3 or toothbrush device 1 with respect to the axis L of the coupler shaft 16. The engaging piece 32 may be referred to as a resilient hook and the fastener mount portion 33 may be referred to as a rigid body.

The holding portion 31 comes into contact with the flat surface 16c of the coupler shaft 16 and lateral parts of the curved surface 16d, as viewed in FIG. 2(c). Further, an opening, or a window 31a, is formed above the holding portion 31 in the brush member 3. The window 31a provides communication with the electric terminal accommodation chamber 23, at the rear side of the toothbrush device 1, that is, the side facing toward the electric terminal plate 24. The curved surface 16d of the coupler shaft 16 comes into contact with the contact 24a of the electric terminal plate 24 through the window 31a. The holding portion 31 includes a step 31b, which comes into contact with the distal end surface of the coupler shaft 16, as shown in FIG. 2(a).

Referring to FIGS. 2(a) and 2(b), the engaging piece 32 is an arcuate thin plate formed in conformity with the outer surface of the coupler shaft 16. The engaging piece 32 extends parallel to the axis L of the coupler shaft 16 to the basal end of the brush member 3. The engaging piece 32 is arranged at a side of the axis L of the coupler shaft 16 at which a contact portion C defined between the coupler shaft 16 and electric terminal plate 24 is located, that is, at the rear side of the brush member 3 or toothbrush device 1. The engaging piece 32 has a distal end, which defines a hook 32a. The hook 32a engages the annular groove 16b of the coupler shaft 16. The engaging piece 32 is snap-fitted to the coupler shaft 16. Further, the engaging piece 32 has a basal portion located near the holding portion 31. The basal portion of the engaging piece 32 is supported by two supports 32b extending inward from a wall 3b of the brush member 3. A clearance is provided at the rear side of the engaging piece 32 so as to allow for resilient deformation of the engaging piece 32. The engaging piece 32 is deformed during insertion of the coupler shaft 16 into the receptacle 22. Upon completion of the insertion, the engaging piece 32 becomes engaged with the annular groove 16b and resiliently returns to its substantially original shape. The resiliency of the engaging piece 32 forces the longitudinal middle part of the coupler shaft 16 toward the rigid fastener mount portion 33, that is, toward the front.

The fastener mount portion 33 is supported by a plurality of supports 3c, which extend inward from the wall 3b of the brush member 3. Further, the fastener mount portion 33 is arcuate and formed in conformity with the outer surface of the coupler shaft 16. The fastener mount portion 33 is formed at a position facing toward the engaging piece 32.

In the illustrated embodiment, the contact portion C defined between the coupler shaft 16 and the electric terminal plate 24 is located at the rear side of the brush member 3 or the toothbrush device 1 with respect to the axis L of the coupler shaft 16. The fastener mount portion 33 is located at the front side of the brush member 3 or the toothbrush device 1 with respect to the axis L of the coupler shaft 16. The engaging piece 32 is located at the same side as the contact C, and the fastener mount portion 33 is located opposite to the contact portion C. This arrangement stably attaches the brush member 3 to the coupler shaft 16 and prevents rattling of the brush member 3.

If the engaging piece 32 and the fastener mount portion 33 were to exchange positions, deformation of the engaging piece 32 would result in the brush member 3 tending to incline toward the front with respect to the coupler shaft 16. Thus, such an arrangement is not preferable. With regard to this aspect, in the illustrated embodiment, the holding portion 31 prevents the distal portion of the coupler shaft 16 from moving forward even when the engaging piece 32 is deformed. This prevents the brush member 3 from being inclined relative to the coupler shaft 16. This also prevents rattling of the brush member 3.

When a person holds the grip 2 and uses the toothbrush device 1, the human body and the toothbrush device 1 form a closed circuit. As a result, the battery 12 sends a very weak current into the mouth via the shafts 15 and 16 and the electric terminal plate 24. This improves the plaque removal effect.

The illustrated embodiment has the advantages described below.

(1) In the toothbrush device 1, the receptacle 22 of the brush member 3 supports the distal portion of the coupler shaft 16 at a section opposite to the contact portion C that contacts the electric terminal plate 24. The inlet of the receptacle 22 includes the engaging piece 32, which is engaged with the coupler shaft 16 due to its resiliency after insertion of the coupler shaft 16 into the receptacle 22, and the fastener mount portion 33, which faces toward the engaging piece 32. The coupler shaft 16 is held between the engaging piece 32 and the fastener mount portion 33. The engaging piece 32 of the receptacle 22 and the contact portion C are arranged at the same side of the axis L of the coupler shaft 16. For example, both of the engaging piece 32 of the receptacle 22 and the contact portion C are arranged at the rear side of the brush member 3 or toothbrush device 1. The fastener mount portion 33 is arranged opposite to the contact portion C with respect to the axis L of the coupler shaft 16. For example, the fastener mount portion 33 is arranged at the front side of the brush member 3 or toothbrush device 1 while the contact portion C is arranged at the rear side of the brush member 3 or toothbrush device 1. Such an arrangement prevents the distal portion of the coupler shaft 16 from displacing toward the electric terminal plate 24 and prevents inclination or rattling of the brush member 3.

(2) In the toothbrush device 1, which includes the drive unit for reciprocating the coupler shaft 16 in the grip 2, the brush member 3 is prevented from rattling.

It should be apparent to those skilled in the art that the present invention may be embodied in many other specific forms without departing from the spirit or scope of the invention. Particularly, it should be understood that the present invention may be embodied in the following forms.

In the illustrated embodiment, the distal portion of the coupler shaft 16 has a D-shaped cross-section, and the curved surface 16d comes into contact with the electric terminal plate 24. However, the present invention is not limited to such a structure. For example, the coupler shaft 16 may be inserted into the receptacle 22 so that the flat surface 16c faces toward the electric terminal plate 24. In this case, the flat surface 16c comes into contact with the electric terminal plate 24. Further, in addition to a D-shaped cross-section, the distal portion of the coupler shaft 16 may have any crosssectional shape. For example, the distal portion may have a round cross-section.

In the illustrated embodiment, the coupler shaft 16 comes into contact with the electric terminal plate 24 at the rear side of the brush member 3 or the toothbrush device 1. However, the present invention is not limited to such a structure. For example, the coupler shaft 16 may come into contact with the electric terminal plate 24 at the front side of the brush member 3 or the toothbrush device 1.

In the illustrated embodiment, the present invention 1S applied to the electric toothbrush device 1. However, the present invention may be applied to a non-electric toothbrush.

The present examples and embodiments are to be considered as illustrative and not restrictive, and the invention is not to be limited to the details given herein, but may be modified within the scope and equivalence of the appended claims.

What is claimed is:

1. A toothbrush device comprising:
a grip including a coupler shaft and a power supply;
a brush member including a receptacle for receiving the coupler shaft for connection with the grip, wherein the brush member further includes an electric terminal accommodation chamber and an electric terminal plate accommodated in the electric terminal accommodation chamber, the electric terminal plate includes a contact, which comes into contact with a contact portion of the coupler shaft through a window providing communication with the receptacle, and the electric terminal plate is supplied with power from the power supply through the contact and the coupler shaft;
the brush member includes a holding portion which supports the coupler shaft at a side opposite the contact portion in the receptacle;
the receptacle has an inlet including an engaging piece, which upon completion of insertion of the coupler shaft resiliently returns to substantially its original shape and engages the coupler shaft, and a fastener mount portion, which faces toward the engaging piece, and the engaging piece cooperates with the fastener mount portion to hold the coupler shaft therebetween; and
the engaging piece and the contact portion are arranged at the same side of an axis of the coupler shaft, and the fastener mount portion is arranged opposite the contact portion with respect to the axis of the coupler shaft.

2. The toothbrush device according to claim 1, wherein the grip includes a drive unit which reciprocates the coupler shaft along the axis of the coupler shaft.

3. The toothbrush device according to claim 1, wherein the fastener mount portion and the holding portion are arranged at the same side of the axis of the coupler shaft.

4. The toothbrush device according to claim 1, wherein:

the brush member has a front side including a brush;

the fastener mount portion is arranged at the front side with respect to the axis of the coupler shaft; and the engaging piece and the contact portion are arranged at a rear side, which is opposite to the front side, with respect to the axis of the coupler shaft.

5. The toothbrush device according to claim 4, wherein the fastener mount portion and the holding portion are arranged at the front side with respect to the axis of the coupler shaft.

6. The toothbrush device according to claim 4, wherein the engaging piece is a resilient hook, and the fastener mount portion is a rigid body.

* * * * *